US012222353B2

(12) United States Patent
Maroun Cortez

(10) Patent No.: US 12,222,353 B2
(45) Date of Patent: Feb. 11, 2025

(54) CRUDE NATIVE HAPTEN-BASED INDIRECT ELISA ASSAY KIT AND LYOPHILISED CONTROLS FOR THE CONFIRMATORY DIAGNOSIS OF BOVINE BRUCELLOSIS IN BLOOD SERUM AND MILK BY ANIMAL AND TANK

(71) Applicant: Victoria Maroun Cortez, Coahuila (MX)

(72) Inventor: Victoria Maroun Cortez, Coahuila (MX)

( * ) Notice: Subject to any disclaimer, the term of this patent is extended or adjusted under 35 U.S.C. 154(b) by 419 days.

(21) Appl. No.: 16/603,019

(22) PCT Filed: Apr. 5, 2018

(86) PCT No.: PCT/MX2018/050009
§ 371 (c)(1),
(2) Date: Oct. 9, 2020

(87) PCT Pub. No.: WO2018/186731
PCT Pub. Date: Oct. 11, 2018

(65) Prior Publication Data

US 2021/0025888 A1 Jan. 28, 2021

(30) Foreign Application Priority Data

Apr. 6, 2017 (MX) ................... MX/A/2017/004490
Apr. 5, 2018 (MX) ................... MX/A/2018/004219

(51) Int. Cl.
*G01N 33/573* (2006.01)
*G01N 33/569* (2006.01)

(52) U.S. Cl.
CPC ... *G01N 33/56911* (2013.01); *G01N 2333/23* (2013.01)

(58) Field of Classification Search
None
See application file for complete search history.

(56) References Cited

PUBLICATIONS

Alonso-Urmeneta et al (Clin. And Diag. Lab. Immunol. 1998, vol. 5 (6): 749-754).*
Diaz et al (Ann Rech Vet . 1981;12(1):35-9).*
Moreno et al (IInfect. Immun. Nov. 1987. 55(11): 2850-2853).*
Ramirez-Pfeifer et al (Clin. Vacc. Immunol. Jun. 2008. 15(6): 911-915).*

* cited by examiner

*Primary Examiner* — Jennifer E Graser
(74) *Attorney, Agent, or Firm* — Armstrong Teasdale LLP

(57) ABSTRACT

A diagnostic kit for a confirmatory assay using the indirect ELISA method that measures the levels of anti-Native Hapten antibodies produced during a real infection, thereby preventing large financial losses to livestock farm, by discerning "false positives" that present anti-LPS antibodies due to cross-reactions with enterobacteria and post-vaccinal antibodies for the diagnosis of bovine brucellosis in blood serum and individual milk (per animal) and bulk milk (tank), characterised by using the crude Native Hapten antigen, extracted from *B. melitensis* 16M strain, with no purification treatment and an effective adherence capacity, which is used to antigenize plates at a known concentration (1 μg per well), where using as reference positive and negative controls subjected to the lyophilisation (freeze drying) method to ensure their preservation, thereby avoiding the contamination and degradation of the antibodies present and ensuring the stability of the optical densities in said controls for a correct results interpretation of an indirect ELISA, are taken as reference. The lyophilisation method for controls that may be used in other diagnostic methods is also presented.

2 Claims, 5 Drawing Sheets

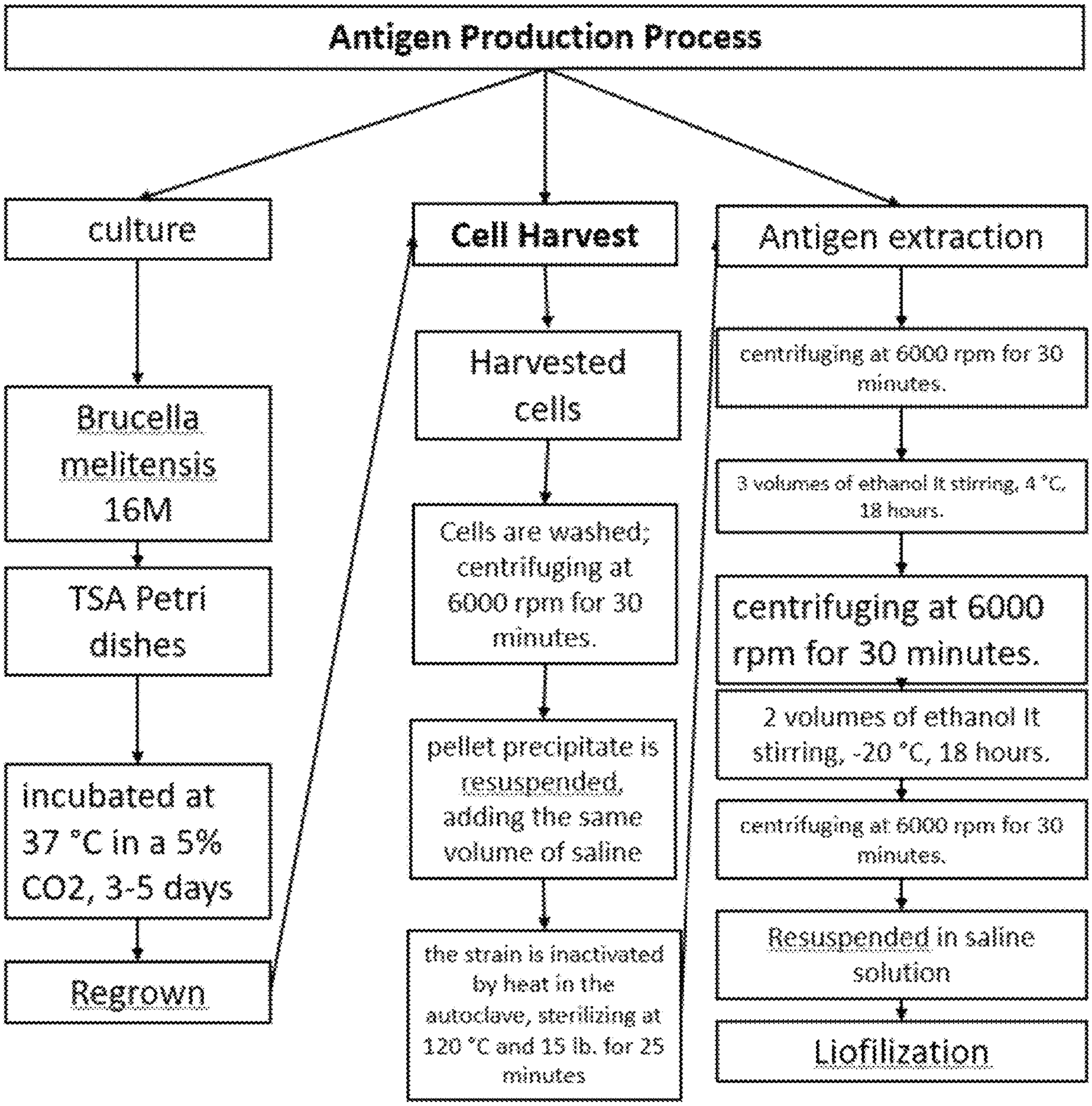

FIGURE 1.

```
                    Antigen Production Process
                    ┌──────────┬──────────┐
                    │          │          │
                 culture   Cell Harvest   Antigen extraction
                    │          │          │
                    ▼          ▼          ▼
               Brucella    Harvested    centrifuging at 6000 rpm for 30
               melitensis    cells      minutes.
                 16M          │          │
                    │         ▼          ▼
               TSA Petri  Cells are washed;  3 volumes of ethanol lt stirring, 4 °C,
                dishes    centrifuging at    18 hours.
                    │     6000 rpm for 30    │
                    ▼     minutes.           ▼
              incubated at   │          centrifuging at 6000
              37 °C in a 5%  ▼          rpm for 30 minutes.
              CO2, 3-5 days  pellet precipitate is  │
                    │        resuspended,           ▼
                    ▼        adding the same   2 volumes of ethanol lt
                Regrown      volume of saline  stirring, -20 °C, 18 hours.
                             │                 │
                             ▼                 ▼
                        the strain is inactivated  centrifuging at 6000 rpm for 30
                        by heat in the             minutes.
                        autoclave, sterilizing at  │
                        120 °C and 15 lb. for 25   ▼
                        minutes              Resuspended in saline
                                             solution
                                                   │
                                                   ▼
                                             Liofilization
```

| | N° anim | % |
|---|---|---|
| TOTAL MILKING COWS | 2533 | 100.00% |
| TRADITIONAL TEST NEGATIVE ANIMALS | 1792 | 70.75% |
| TRADITIONAL TEST POSITIVE ANIMALS | 741 | 29.25% |
| FALSE POSITIVE SERO REACTOS | 386 | 15.24 % |
| INFECTED ANIMALS (CONFIRMED BY THIS KIT) | 355 | 14.02% |

CRUDE NATIVE HAPTEN-BASED INDIRECT ELISA ASSAY KIT AND LYOPHILISED CONTROLS FOR THE CONFIRMATORY DIAGNOSIS OF BOVINE BRUCELLOSIS IN BLOOD SERUM AND MILK BY ANIMAL AND TANK

Raw Native Hapten-based indirect ELISA assay KIT and lyophilized controls for confirmatory diagnosis of bovine brucellosis in blood serum and individual and tank milk.

DESCRIPTION

Object of the Invention

The indirect enzyme-linked immunosorbent assay of anti-NH ELISA is a test that is fundamentally based on the determination of IgG isotype antibodies against the *Brucella* antigen named Native Hapten (NH) in samples of blood serum, whole milk and/or whey, being either, individual or bulk milk samples, with the ability to distinguish infected animals from those animals with temporary exposure to *Brucella* spp. This product is exclusive for veterinary use for in vitro diagnostic in bovines.

The novelty of this invention is the development of a diagnostic kit based on the detection of antibodies against the Native Hapten antigen of *Brucella*, using the Indirect ELISA method. This kit includes microplates coated with the Native Hapten antigen in its raw form, the washing solutions, the sample diluent, the conjugate diluent, the substrate, the stop solution and the positive and negative controls, previously submitted to a lyophilization process, which are specific for blood serum and bovine milk.

BACKGROUND

The present invention is related to the biotechnological area, specifically for brucellosis detection in cattle through detection of reactive antibodies against the Native Hapten (NH) antigen of *Brucella*. Nowadays, brucellosis is an infectious disease that affects livestock and humans; it is caused by Gram-negative coccobacilli of the genus *Brucella*. It is cataloged as an important bacterial disease with a high impact on public health, since every year are reported about 500,000 new cases worldwide; it also decreases milk production, delays the growth of calves, causes abortions and produces reproductive problems in females, which is reflected in their production.

In Mexico, it is considered the most important bacterial zoonosis, being *Brucella abortus* the species that mainly affects cattle. The control of the disease depends on the NOM-041-ZOO-1995, National Campaign against Brucellosis in Animals application. The fundamental strategy of the campaign is based on diagnosis and vaccination.

In Mexico cattle immunization is carried out with strains S19 and RB51 of *Brucella abortus*, S19 induce the presence of antibodies in serum and milk that interfere with the tests remarked as officials, thus, strain RB51 has been used as an alternative [4, 5, 6, 7, 8, 9]. Regarding serological diagnostic methods, the most commonly used are the Rose Bengal Test (RBT) and Rivanol test for blood serum and for milk samples is used the Milk Ring Test (MRT), which are considered as officials in NOM-041-ZOO-1995 [2, 10]. These tests detect antibodies against the *Brucella*'s outer membrane components, mainly directed against the O chain of Lipopolysaccharide (LPS) which is the most antigenic structure of smooth strains. Therefore, it is the first antigen against which antibodies are produced, however, these antibodies are present both in the infection and in vaccination, also, given the cross-reactivity present between *Brucella*'s LPS and other Gram-negative bacteria's LPS, contact with brucellosis animals, productive stress and even the environmental factors, it is frequent the appearance of false positives results [11, 12, 13, 14, 15].

In the International Organization of Epizootics (OIE) manual on Bovine Brucellosis in terrestrial animals, the interferon gamma tests, the immunoprecipitation test that uses Native Hapten, and the indirect ELISA that used the rough lipopolysaccharide as antigen are highlighted as promising tests to differentiate between brucellosis infection and exposure to cross-reactive microorganisms; the manual also highlights the indirect ELISA test or the ring milk test, with whole milk samples, as effective tests to analyze and control brucellosis in dairy cows. However, no serological test is considered adequate for each and every epidemiological situation. Therefore, samples that are positive in the analysis tests must be confirmed using an established confirmatory strategy [16]. For this reason, alternative tests with antigens different from LPS have been developed to decrease this reactivity and grant higher specificity levels.

The LPS electrophoretic analysis allows the identification of a second component, the Native Hapten (NH), called second polysaccharide or poly-B, but for representing with certainty the equivalent in the *Brucella* genus of the native haptens of other Gram-negative bacteria, currently it is called as NH [17]. It is chemically identical to the O chain, in *B. melitensis*, the O chain consists of repeated units of five N-formylperosamine residues, four linked to α-1,2 and one bound to α-1,3 [18]. It is an intracellular antigen, located in the periplasmic space, of a non-proteic nature and low molecular weight; properties that make it less antigenic, the appearance of precipitating antibodies in animal serum depends on the intensity of its antigenic stimulus. That is, antibodies against NH will be produced only when the immune system is exposed to the antigen for a long time, as in the case of an infection and not by vaccination [4, 14, 19, 20, 21, 22].

Native Hapten has been studied over years, in which its efficiency has been described in several studies applied in different species and with different methods. In 1981, a Radial Immunodiffusion (RID) test was carried out on blood serum of cattle, describing the obtaining method of Native Hapten antigen from a *B. melitensis* 16 M strain cultured in Tripticasein Soy Broth for 48 h at 37° C. and inactivated with phenol 0.5%, in addition, it was washed with saline solution and resuspended in distilled water. In this method, the extraction was carried out with 3 and 2 volumes of ethanol in which the antigen obtained was purified and tested by the previously mentioned method in blood serum of bovines [23].

For brucellosis diagnosis in humans, an indirect ELISA with NH was developed in 1986. The NH extracted from *B. melitensis* 16M by ethanol precipitation, the purified and freeze dried antigen was adhered to the ELISA plates (for 12 h at 37° C.) at a 2 μg per well concentration, known quantities of blood serum were placed (100 μl), anti-human (goat) IgG, IgA, IgM and 1N NaOH were used as conjugate and stop solution respectively. The results shown describe a 99% effectiveness in anti-NH IgG detection in patients positive for the disease [24]. There are reports of studies made in Spain (1988) that uses native hapten in a competitive ELISA for bovine brucellosis where the antigen extraction is carried out as in the previous references, from *B. melitensis* 16M cultured in Soy Tripticaseina agar (TSA) to then perform two ethanol precipitates to obtain the crude NH antigen which is then purified by a long process for its subsequent lyophilization. After coating the ELISA plates with antigen (over night 37° C.), 50 µl of blood serum or whey is added to each well, plus 50 µl of a heterologous molecule giving a total of 100 µl of sample per well for the formation of the antigen-antibody Ag—Ac complex by competition, which react with the secondary antibody (anti-rabbit IgG [goat]) and a substrate, the reading is made at 450 nm of the results allows to evaluate the efficacy of the antigen [(25)].

With the RID test, in 1993 the NH antigen extracted as described before was used by Diaz R, et al. (1981) and it was purified by a long process of dialysis and digestion, it was proved that it was possible to differentiate cattle and sheep infected from vaccinated with a sensitivity and specificity very similar to that of complement fixation test (CFT)[26]. In 1994 the effectiveness of NH was once again demonstrated in blood serum of goats, through an indirect ELISA in which different strains of *Brucella* were used, such as *B. melitensis* 16M, 115, *Rev* 1; *Brucella abortus* 2308. These strains were cultivated in broth with stirring and for its harvest; the cells were washed with saline solution and resuspended in distilled water. The extraction of phenol inactivated and sterilized antigen was performed with 3 and 2 volumes of ethanol. It was purified by digestion with nucleases and proteinase K, extracted with phenol and precipitated with ethanol, the crude extract was used to coat the ELISA plates at a concentration of 0.25 µg per well, incubating over night at 4° C. The goat blood sera were tested by this method, placing 100 µl (diluted serum) per well, where polyclonal goat anti-goat (rabbit) and recombinant protein G were used as secondary antigen options. The reading at 405 nm of the samples showed that NH ELISA in goats presents 60% specificity [(27)].

Another study reported in 1996 the sensitivity of the RID test for the detection of anti-NH antibodies in sheep blood serum was tested, comparing the NH extracted from different species of *Brucella* and *Yersinia* (*Brucella melitensis* M16, *Rev* 1, *Brucella abortus* 2308, *Yersinia enterocolitica O:* 9) grown in TSB broth, in which it was concluded that the sensitivity of the test is greater when using the NH (purified and freeze dried) of *B. melitensis* 16M [(28)]. In a comparative study between *Brucella* polysaccharides in an indirect ELISA in sheep and cattle using *B. abortus* 2308 and *B. melitensis* 16 M strains cultivated in a fermentor, it was concluded that for unspecified reasons, the Native Hapten is not the optimal antigen for the brucellosis diagnosis for this type of tests [(29)]. In 1999, a comparative study was carried out in Spain between a competitive ELISA, an indirect ELISA and the Rose Bengal test (RBT) where all three tests used LPS, against the Radial Immunodiffusion Test using NH (AGID-NH) extracted from a *B. melitensis* 16M strain, based on the extraction method described by Diaz R, et al. (1981), based on the results obtained, it was concluded that using the RBT as a screening and with AGID-NH as confirmatory test, was an effective system to diagnose brucellosis in sheep, this same scheme was used for brucellosis eradication in cattle in the same country [(30)]. In 2005, a group of researchers conducted an indirect ELISA study with NH in bovines, where favorable results were obtained using the NH extracted from *B. melitensis* 16M at a concentration of 2.5 µg/ml of antigen per well, taking as reference the methods described by Diaz R, et al. (1981) and Urmeneta B, et al (1998) [(31)]. Likewise, in more recent studies, patent WO2008051065 A1, from May 2, 2008 reports a fluorescence polarization assay (FPA) using the NH of *B. melitensis Rev* 1, a strain that has been used previously, which was cultured on *Brucella* agar and inactivated with phenol, in which the NH was extracted with ethanol, dialyzed and purified for the detection of anti-NH antibodies in goats [(32)].

In order to make the confirmatory diagnosis of brucellosis more efficient and to avoid the "false positive" emitted by the existing tests based on the detection of anti-lipopolysaccharide antibodies (anti-LPS) and other inconveniences such as cross-reactions with enterobacteria, and post-vaccinal reactions, it was thought to develop the present test, which is intended to be protected by means of the present application, since it is an indirect ELISA test that is more efficient in its application and a suitable kit for detecting the presence of anti-Native Hapten antibodies, which only occur during a true brucellosis infection.

DETAILED DESCRIPTION OF THE INVENTION

It is a novel invention for brucellosis diagnosis, because due to the expression of antibodies against Native Hapten only occurs during a field infection, this test allows to discriminate between truly positive animals from the false positives, ensuring that the animals sent to slaughterhouse correspond only to the infected animals. It avoids the presence of false negative animals within the healthy population, preventing the spread of the disease. Besides, to being used in blood serum, this test can also be used for milk analysis, a novel feature since there are no reports on diagnostic tests that use NH in milk. This test can be used using individual cow milk or bulk milk, with a detection capacity of 969.162 liters of positive milk in a tank of 30,000 liters, proving to be a highly sensitive and specific test. For all the mentioned before, this test can be taken as a tool that contributes to the eradication of the disease thus preventing the spread to humans.

1.—Antigen Production

*Brucella melitensis* 16M cultivation

The production of the antigen is carried out in an isolated area, using biosecurity measures typical of a microbiology laboratory (biosecurity level 2). The equipment used in the area consists of a CO2 incubator, centrifuge, autoclave, refrigerator, Fischer burners and analytical scale. The first culture is done from the *Brucella melitensis* 16M strain preserved in liquid nitrogen using the streak plate technique in a Petri dish with trypticase soy agar (TSA). The Petri dish is incubated at 37° C. in a 5% CO2 incubator for 72 to 120 hours. As the colonies grow on the dish they should be checked against light, a bluish color should be observed, characteristic of *B. melitensis* strain. These colonies are regrown (re-cultivated) on new Petri dishes with TSA medium to start a new production batch. Subsequently, they are incubated under the same incubation conditions mentioned before. Of those ten dishes, those that do not present contamination are selected to be regrown in approximately 80 new Petri dishes and are incubated under the same conditions.

Cell Harvest

After the incubation time the cells within the 80 Petri dishes are harvested using a cell scraper or a pasteur pipette bent into an L shape and placing the cells into a Falcon tube with 10 ml of sterile saline solution, the volume of saline may vary according to the amount of cells harvested. The cells are washed; centrifuging at 6000 rpm for 30 minutes. The supernatant obtained is discarded and the pellet precipitate is resuspended, adding the same volume of saline as previously added. The washings continued until the supernatant obtained is clear. At the end of the washings, the strain is inactivated by heat in the autoclave, sterilizing at 120° C. and 15 lb. for 25 minutes.

Extraction

Wait for it to cool down and perform a centrifugation at 6000 rpm for 30 minutes. The supernatant is taken with a syringe to control the volume obtained. This should be taken on the opposite side of the pellet to avoid contamination. The supernatant is poured into a 100-500 ml beaker, depending on the volume obtained. Three volumes of cold ethanol are added to the supernatant (example: if 10 ml of supernatant are contained in the beaker, 3 volumes of 10 ml of ethanol must be added). It is placed in magnetic stirring, maintaining it at 4° C. for 18 hours to precipitate the antigens. It is then centrifuged at 6000 rpm for 30 minutes, take the pellet and resuspend in saline, adding 0.5 ml, mix and observe the turbidity, if it is observed too saturated you can add 0.5 ml more, avoiding to reach transparency as this could dilute the antigen so that a low concentration of it will be obtained, this is labeled as LPS antigen. Two more volumes of cold ethanol are added to the supernatant, and it is kept in freezing (−20° C.) for 18 hours without agitation to precipitate the NH antigen. When finished, centrifuge at 6000 rpm for 30 minutes. The formed pellet is taken and resuspended in 0.5 ml of saline, observe the turbidity, add more saline solution if necessary. This suspension contains the NH antigen.

Lyophilization of Raw Native Hapten Antigen

The lyophilization (or freeze drying) of the antigen and controls is carried out in an exclusive area for this procedure. The area in general has a negative pressure preventing possible contamination to adjacent areas. The equipment consists of a freeze dryer and a freezer. After the antigen extraction is completed, aliquots of the NH suspension are made in glass vials of the same size, placing 1 ml in each previously labeled vial. The vials are frozen at −80° C. for 30 minutes to 1 hour, placing the stoppers of the vials half-closed to facilitate the extraction of the vacuum. After freezing the vials are placed in the trays of the freeze dryer balancing the amount of vials on each side. The pressure and temperature of the freeze dryer is monitored during the process, the temperature should be about −80° C. The lyophilization process should be carried out for at least 6 hours. At the end of lyophilization, the vials should be capped and sealed. To open the vials, gently puncture the cap until you see that the antigen stops releasing pressure to prevent the antigen from being lost due to the release of the vacuum. 2 mg of the antigen are weighed and passed to microtubes properly identified. The vials with antigen can be stored in refrigeration at 4° C. until use. The processes for antigen production are shown in FIG. 1.

2.—Microplate Coating

The coating of the plates is carried out in an isolated area inside a type II biosafety cabinet, incubator and refrigerator. The area in general should have a slightly positive pressure. There are ten (10) coated microplates of 96 wells contained in the kit, the wells are distributed in 12 strips of 8 wells each, the material of the microplates is polystyrene with a specially treated surface (by the manufacturer) for achieving a high capacity of adhesion of the antigen, with a maximum capacity of 360 microliters per well, flat and clear bottom. The coating procedure is as follows: A microtube with 2 mg of the freeze dried Native Hapten antigen is reconstituted with 1 ml of sterile distilled water, making sure to dissolve all the freeze dried content. Once dissolved, the milliliter is added in 99 ml of bicarbonate carbonate buffer solution (CABI) to obtain a total of 100 ml (20 μg/ml), and it is mixed perfectly. To each well of the microplates is added 50 μl (1 μg of antigen) of this solution and sealed with parafilm. The microplates are incubated at 4° C. for 18 hours (Overnight).

The microplates are washed with a 0.05% PBS-Tween 20 washing solution by adding 250 μl of this solution to each well and discarding it immediately. The washings are done 4 times. The excess of the washing solution is removed by shaking the plate twice and gently tapping it on a flat surface covered with a disposable towel. Subsequently, 50 μl of blocking solution (3% skim milk) is added to each well and the microplates are sealed. They are incubated at 37° C. for 1 hour and at the end another series of four washes are carried out as mentioned above. The excess solution is removed from the microplates and covered with the plastic microplate adhesive cover. They are sealed in a plastic bag by removing the vacuum, placing 10 plates in each bag labeled with the product name, batch number, date of manufacture and expiration date. The microplates are stored in refrigeration at 2-8° C. The process mentioned above is described in FIG. 2.

3.—Procedure of the Indirect ELISA Anti-NH

Preparation of Samples

Before being analyzed, the samples should be diluted to a concentration of 1:20 with the Sample Diluent solution (CABI buffer), using a pre-dilution Microplate.

Blood Serum:

Blood samples are left to coagulate, and are centrifuged at 2500 rpm for 10 minutes. In samples taken from 12-24 hours prior to the test, it is not necessary to centrifuge. Samples with fibrin debris should be centrifuged before the test. Highly hemolyzed or lipemic samples should not be processed. The samples are stable for 2 days stored at 2-8° C. or 3 months at −20° C.

Milk:

Milk samples can be processed as whole milk, by shaking the sample before adding it in the pre-dilution plate, or it can be added as whey. To obtain whey, the samples are centrifuged at 2500 rpm for 15 minutes and then the top layer containing fat is removed using an applicator. The sample is stable 3 days at 2-8° C. or 3 months at −20° C.

Preparation of ELISA Reagents

The preparation of washing and diluting solutions is carried out in an isolated area within a laminar flow hood. The weighing of the reagents is carried out using an analytical scale and the pH adjustment is made out with a potentiometer. The area in general should have a slightly negative pressure.

Sample Diluent Solution. Bicarbonate Carbonate Buffer (CABI):

Dilute the 10× Sample Diluent solution in a 1:10 rate in distilled water. Example, to prepare 30 mL, dilute 3 mL of solution in 27 mL of distilled water.

Washing Solution. PBS-TWEEN 20 (0.05%):

Dilute the 10× Wash Solution in a 1:10 rate. Example, to prepare 250 mL, dilute 25 mL in 225 mL of distilled water.

Concentrated Conjugate:

The conjugate is an anti-bovine IgG produced in goat conjugated with horseradish peroxidase. Dilute the Concentrated Conjugate to a 1:50 rate using the Conjugate Diluent Solution. The conjugate should be diluted 15 minutes before being used. Once diluted, the concentration of the conjugate is 1:2000 and cannot be stored again. Example, to prepare 5 mL, dilute 100 μl of Concentrated Conjugate in 4.9 mL of Conjugate Diluent Solution.

Stop Solution. SDS 4%:

It is recommended to keep the solution at room temperature to avoid the formation of crystals before its use. In case of crystallization, temper the solution at 37° C. and homogenize correctly, 30 minutes before its use. Do not shake the solution immediately before using, to avoid the formation of bubbles.

Positive and Negative Controls of Blood Serum and Milk Whey:

The production of controls is carried out in the process area, which consists of a spectrophotometer, an automated plate washer, an incubator at 37° C., a centrifuge, micropipettes of different volumes of capacity, and refrigerator. In this area, individual sera are selected to later elaborate pools. The following tests are performed for blood serum: RBT, Rivanol, RID, BruScreen anti-LPS ELISA and BruPlus anti-Native Hapten ELISA; and for milk serum: MRT, BruScreen anti LPS ELISA and BruPlus anti-Native Hapten ELISA are performed. The controls are freeze dried as a conservation method. The controls are freeze dried so they must be resuspended by adding 1 ml of sterile tridestilated or distilled water, and shaking gently until completely homogenize. Once reconstituted store the controls in refrigeration at 2 to 8° C. It is recommended to make aliquots of the controls and store in freezing those that are not in use, to avoid contamination.

Indirect ELISA Process

It is necessary to keep all the included solutions at room temperature (21° C.±5° C.) and mixing before using. If the reconstituted controls were frozen they should be thawed completely and shaken perfectly before use. Distribute 285 μL of Sample Diluent Solution to each well in the pre-dilution Microplate. Add 15 μL of Negative Control in wells A1 and B1; and 15 μL of Positive Control in wells C1 and D1. Continue adding 15 μL of the sample (blood serum or milk) in the remaining wells. Take 50 μL of the diluted samples and controls in the pre-dilution Microplate (making sure to perfectly mix the samples and controls) and transfer them to the Microplate coated with Native Hapten, being careful to respect the order of the samples. Incubate the coated microplate for 1 hour at 37° C. Subsequently, wash each well with 250 μL of the previously diluted Washing Solution, avoiding the drying of the wells between each wash. Make a total of 4 washes. Remove the excess of Washing Solution by shaking the plate twice and gently tapping it on a flat surface covered with a disposable towel. Add 50 μL of the previously diluted Conjugate (dilution 1:2000) to each well. Incubate the Microplate for 1 hour at 37° C. Perform 4 more washes as mentioned above and remove the excess of washing solution. Add 50 μL of Substrate (ABTS) to each well, being careful not to expose the Substrate to the light, cover the Microplate with aluminum foil to avoid exposing the reaction to light. Incubate the Microplate for 15 minutes at room temperature (20° C.-25° C.) in darkness. Finally, distribute 50 μL of Stop Solution and read at 405 nm of optical. The reading is stable for 30 minutes once the Stop Solution has been added. The procedure is described in FIG. 3.

4.—Selection and Lyophilization of Positive and Negative Controls of Blood Serum and Milk Serum (Whey).

Blood Serum and Milk Localization for Producing Controls

Negative: Are selected from samples of blood serum and milk processed with anti-NH ELISA, those that register an absorbance range of 0.20-0.28. Aliquots of the selected blood serum are made in a previously identified Eppendorf microtube. The aliquots are stored in freezing. In the case of milk, the samples must be skimmed first, centrifuging at 2500 rpm for 15 minutes and removing the top layer containing fat with an applicator. Once skimmed, the aliquots are made and stored in freezing.

Positive: Are selected from samples of blood serum and milk processed with anti-NH ELISA, those that register an absorbance of ≥1.0 nm. Aliquots of the selected blood serum are made and stored in freezing. In the case of milk, the procedure is followed before described.

Pre-Selection of Controls

Frozen Sera should be refrigerated at 2-8° C. before thawing to avoid a sudden change in temperature. Once defrosted, they are removed from the refrigerator and left to cool at room temperature. The samples of blood serum are processed to the official tests (RBT and Rivanol) and RID. And milk samples are tested with MRT. Once these preselected samples are approved, pools of positive and negative sera are formed.

Positive and Negative Control Pools Validation

The pools are validated once again with the official tests, RID and with the anti-LPS ELISA and anti-NH ELISA. Approved pools proceed to lyophilization process and with a previously assigned lot number.

Lyophilization of Positive and Negative Blood Serum and Milk Serum (Whey) Controls.

The control pools should be aliquoted in glass serum vials of the same size, placing 1 ml in each vial, previously labeled. Frozen at −80° C. for 30 min to 1 hour. Afterwards, they are placed in the freeze dryer trays, balancing the amount of vials in each side of the tray. Pressure and temperature are monitored during the process; the temperature should be about −80° C. The lyophilization process should be carried out for at least 6 hours. Freeze dried controls can be stored under refrigeration at 4° C. until use. Controls election and lyophilization procedures are shown in FIG. 4.

PROCEDURES SIMILAR TO THE INVENTION

A search was made to corroborate the existence of procedures similar to the present invention, finding the following:

Summary of procedures found, similar to the invention.

| Publication date<br>Author (s) | 1<br>1981<br>P. Diaz, etal. | 2<br>1986<br>Luis Fernández<br>Lago, Ramón | 3<br>1988<br>B. Alonso<br>Urmeneta, et al | 4<br>1993<br>Efren Diaz<br>Aparicio, et al. | 5<br>1994<br>Efren Diaz<br>Aparicio, et al. |
|---|---|---|---|---|---|
| Test method | Radial Imunodiffusion test | Indirect ELISA | Competitive ELISA | Radial Imunodiffusion test | Indirect ELISA |
| Species | Bovine | Human | Bovine | Bovine, sheep-goat | Goat |
| Bacteria for antigen production | *Brucella melitensis* M16 | *Brucella melitensis* M16 | *Brucella melitensis* M16 | *Brucella melitensis* M16; *B. abortus* 2308; *B. abortus* 19; *Yersinia enterocolitica* O:9 | *Brucella melitensis* M16 115, Rev 1; *Brucella abortus* 2308; *Yersinia enterocolitica* O:9 |

-continued

| | | | | | |
|---|---|---|---|---|---|
| Culture medium of the *Brucella* | Trypticasein Soy Broth (TSB) | Trypticasein Soy Broth (TSB) | Trypticasein Soy Agar (TSA) | Broth (TSB) | Broth (TSB) |
| Method of culture of the *Brucella* | Broth: incubation 48 hours at 37° C. with stirring | Broth: incubation 48 hours at 37° C. with stirring | PLATE. incubation 2.3 days, at 37° C. | Trypticasein Soy Broth: incubation 48 hours at 37° C. with stirring | Trypticasein Soy Broth: incubation at 37° C. with stirring 200 rpm |
| Pre-harvest inactivation method | 0.5% phenol at 37° C. for 24 hours | 0.5% phenol at 37° C. for 24 hours | 0.5% phenol at 37° C. for 24 hours | 0.5% phenol at 37° C. for 24 hours | does not apply |
| Harvest method of the *Brucella* | Centrifugation at 12000 xg, 30 minutes, 5° C. | Centrifugation at 12000 xg, 30 minutes, 5° C. | Centrifugation at 12000 xg, 30 minutes, 5° C. | Tangential filtration | Tangential filtration |
| Harvest washing technique | 2 washes in saline solution | 2 washes in saline solution | 2 washes in saline solution | 2 washes in saline solution | 2 washes in saline solution |
| Solution to resuspend the harvest | Distilled water | Distilled water | Distilled water | Distilled water | Distilled water |
| Post-harvest inactivation method | Sterilization at 120° C., 30 minutes | Sterilization at 120° C., 30 minutes | Sterilization at 120° C., 30 minutes | Sterilization at 120° C., 30 minutes | Phenol 0.5% at 37° C. to 24 hours. |
| Extraction and Precipitation Method | does not apply | does not apply | Hot water 120° C. | does not apply | Sterilization at 120° C., 15 minutes |
| | Centrifugation at 12000 xg, 30 minutes, 5° C. | Centrifugation at 12000 xg, 30 minutes, 5° C. | does not specify | Centrifugation at 12000 xg, 30 minutes, 5° C. | Centrifugation |
| | 3X-Ethanol for 1.8 hours at 5° C., with stirring | 3X-Ethanol for 24 hours at 4° C. | 3X-Ethanol for 18 hours at 4° C. with stiring | Reference R. Diaz, 1981 | 3X-Ethanol |
| | Centrifugation: 5000 g, for 15 minutes, at 5° C. | Centrifugation: 5000 g, for 15 minutes, at 5° C. | Centrifugation: 5000 g, for 15 minutes, at 4° C. | Reference R. Diaz, 1981 | does not specify |
| | 2X-Ethanol by O/N at −20° C. | 2X-Ethanol by O/N at −20° C. | 2X-Ethanol by O/N at −20° C. | Reference R. Diaz, 1981 | 2X-Ethanol |
| | Centrifugation: 5000 g, for 15 minutes, at 5° C. | Centrifugation: 5000 g, for 15 minutes, at 5° C. | Centrifugation: 5000 g, for 15 minutes, at 5° C. | Reference R. Diaz, 1981 | does not specify |
| Solution to resuspend the NH antigen pellet | Distilled water | Distilled water | does not specify | does not specify | does not specify |
| Purification | Dialysis against distilled water | Filtration in 40 mg chide NH in 2.5 ml Tris HCL | 100 mg of the 2nd precipitate in 50 ml of 4% SDS | Digestion with nucleases, DNAses and RNAse, 18 h 37° C. | Digestion with nucleases and proteinase K |
| | | Chromatography with Sephacryl S300 | Water bath incubation 15 min | Dialysis against 0.1M sodium acetate | Ultra-centrifugation |
| | | PM30 membrane fractionation | Removed LPS complexes with 5% potassium acetate | Digestion with B-D-glucoside glucohydrolase 18 h 37° C. | Phenol Extraction |
| | | Dialysis against distilled water 3 days at 4° C. | Incubation 4° C. for 12 h | Proteinase K 1 h 55° C. 2 times | Ethanol precipitation |
| | | does not apply | Centrifugation: 5000 g, for 10 minutes, at 4° C. | Ultra-centrifugation 6 h, 200,000 g | |
| | | | 5 volumes of ethanol | 1 volume of 70° phenol | |
| | | | was suspended in 150 ml distilled water. | 9000 g 15 min | |
| | | | It was treated twice with 4 g of Dowex 1X4-200 | 5 volumes of ethanol −20° C. overnight | |
| | | | Dialysis | 7 volumes of ethanol −20° C. overnight | |
| | | | Lyophilized | Dialysis | |
| | | does not apply | Dialysis | 7 volumes of ethanol −20° C. overnight | |
| | | | Lyophilized | Dialysis | |
| | | | Solution in 10 mM borate-NaOH | | |
| | | | Chromatography 10 ml per h, column P300 bio gel with borate | | |

-continued

| | | | | | |
|---|---|---|---|---|---|
| | | | buffer<br>Collection of<br>hapten fractions<br>Precipitation<br>with 5 vol<br>Ethano<br>Dialysis | | |
| Lyophilization of the antigen | Yes | Yes | Yes | Yes | does not specify |
| Sensitization | | | | | |
| Antigen concentration per ml of diluent | does not apply | 20 μg/ml | 1-2.5 μg/ml | does not apply | 2.5 μg/ml |
| Diluent | | Barbital acetate pH 4.6, with Na azide 0.02% | 60 mM CABI pH 9.6 | | 10 mM PBS pH 7.2 |
| Volume of antigen dilution per well | | 100 μl | does not specify | | 100 μl |
| Antigen concentration per well | | 2 μg | does not specify | | 0.25 μg |
| 1st incubation | | 12 h 37° C. | Over Night 37° C. | | Over Night 4° C. |
| 1st wash solution | | Sol. Saline, Tween 20 (0.03%) | does not specify | | PSS Tween 20 (0.05%) |
| Number of washes | | 3 | does not specify | | 4 |
| Volume of wash solution per well | | does not specify | does not specify | | does not specify |
| Blocking solution | | does not specify | does not specify | | does not specify |
| 2nd Incubation | | does not specify | does not specify | | does not specify |
| 2nd wash solution | | does not specify | does not specify | | does not specify |
| Number of washes | | does not specify | does not specify | | does not specify |
| Volume of wash solution per well | | does not specify | does not specify | | does not specify |
| Storage | | does not specify | does not specify | | 4° C. |
| Preparation of sample | | | | | |
| Type of sample | Blood serum | Blood serum | Blood Serum/ Milk Serum | Blood serum | Blood serum |
| Sample treatment | does not apply | inactivation of positive sera at 56° C. tor 30 min | does not apply | does not apply | does not apply |
| Sample Predilution | | Yes | Yes | | Yes |
| Sample quantity | | does not specify | does not specify | | does not specify |
| Sample diluent | | PBS pH 7 2-albumine 0.5% | does not specify | | PBS Tween 0.05% |
| Amount of diluent | | does not specify | does not specify | | does not specify |
| Challenge | | | | | |
| Amount of diluted sample per well | does not apply | 100 μl | 50 μl | does not apply | does not specify |
| Competitive Specifications of Competitive ELISA | | | 50 μl of heterologous molecule (concentration 200 μg/ml) | | does nto apply |
| Final volume per well | | 100 μl | 100 μl | | does not specify |
| Incubation | | 1 h 37° C. | does not specify | | 1 h 37° C. |
| Washes | | | | | |
| Wash solution | does not apply | Sol. Saline, Tween 20 (0.05%) | does not specify | does not apply | PBS Tween 0.05% |
| Number of washes | | 3 | does not specify | | 4 |
| Volume of wash solution per well | | does not specify | does not specify | | does not specify |
| Conjugate | | | | | |
| Conjugate | does not apply | IgG, IgA, IgM anti-human (goat) | IgG anti-rabbit (goat) | does not apply | IgG anti-sheep policlonal (rabbit); Recombinant G protein |
| Conjugate diluent | | does not specify | does not specify | | PBS Tween (0.05%) |
| Conjugate Concentration | | 1:600 | does not specify | | IgG: 1:2000; G protein: 0.2 μg/ml |
| Final conjugate volume per well | | 100 μl | does not specify | | 100 μl |
| Incubation | | 1 h 37° C. | does not specify | | 1 h 37° C. |

-continued

| | | | | | |
|---|---|---|---|---|---|
| **Washes** | | | | | |
| Wash solution | does not apply | Sol. Saline, Tween 20 (0.05%) | does not specify | does not apply | does not specify |
| Number of washes | | 3 | does not specify | | does not specify |
| Volume of wash solution per well | | does not specify | does not specify | | does not specify |
| **Substrate** | | | | | |
| Substrate Name | does not apply | 5-AS | 0.09% 5-amino-24 hydroxy benzoic acid | does not apply | ABTS |
| Substrate Diluent | | H2O2 | H2O2 | | 0.05M citrate bufter (pH 4.0) and 0.004% H2O2 |
| Amount per well | | 100 μl | does not specify | | 100 μl |
| Substrate incubation conditions | | 1 h, Ambient temperature in darkness | does not specify | | 15 min, 20° C. |
| **Stop the reaction** | | | | | |
| Stop solution | does not apply | NaOH 1N | does not specify | does not apply | does not specify |
| Quanity | | 0.025 ml | does not specify | | does not specify |
| Stability time | | does not specify | does not specify | | does not specify |
| **Reading of Optical Densities** | | | | | |
| Nanometers | does not apply | 450 | 450 | does not apply | 405 |
| **Lyophilization of controls** | | | | | |
| Optical density for Positive control selection | does not use it | does not use it | does not use it | does not use it | does not use it |
| Optical density for Negative control selection | does not use it | does not use it | does not use it | does not use it | does not use it |
| Use of the lyophilization process for Negative Control and Positive Control | does not use it | does not use it | does not use it | does not use it | does not use it |

Summary of procedures found, similar to the invention.

| Publication date<br>Author (s) | 6<br>1995<br>Efren Diaz Aparicio, et al. | 7<br>1990<br>B. Alonso Urmeneta, et al | 8<br>1999<br>Marin.C.M., et al | 9<br>2005<br>Muñoz, P.M , et al | 10<br>2008<br>Ricardo Fores, et al | INVENTION |
|---|---|---|---|---|---|---|
| Test method | Radial imunodiffusion test | Indirect ELISA | Immunodifhision on Agar Gel (IDAG) | indirect ELISA; Radial Imunodiffusion test | Polarized fluorescence | Indirect ELISA |
| Species | Sheep | Bovine, sheep-goat | Sheep | Bovine | Goat | Bovine |
| Bacteria for antigen production | *Brucella melitensis* M16, Rev 1; *Brucella abortus* 2308; *Yersinia enterocolitica* O:9 | *Brucella melitensis* M16, *Brucella abortus* 2308 | *Brucella melitensis* M16 | *Brucella melitensis* M16 | *Brucella melitensis* M16, Rev 1 | *Brucella melitensis* M16 |
| Culture medium of the *Brucella* | Broth (TSB) Trypticasein Soy | 1.7% casein-0.3% soy-0.5 % yeast extract-0.25% K2HPO4-2% glucose, 0.5% NaCl-0.01% acetate A-butyl antifoam | Reference R. Diaz. 1981 | Trypticasein Soy Broth (TSB) | *Brucella Agar* | Trypticasein Soy Agar (TSA) |
| Method of culture of the *Brucella* | Broth: incubation at 37° C., with stirring | 1.5 liters in Fermenter Biostat, 36 h, 35% O2 | Reference R. Diaz, 1981 | Broth: incubation 48 hours at 37° C. with stirring | PLATE: incubation 48 hours, at 37° C. | PLATE: incubation 3-5 days, at 37° C. 5% CO2 |
| Pre-harvest inactivation method | does not apply | 0.5% phenol at 36° C. For 48 hours | Reference R. Diaz, 1981 | does not specify | 0.5% phenol at 37° C. for 24 hours | does not apply |

-continued

| | | | | | | |
|---|---|---|---|---|---|---|
| Harvest method of the *Brucella* | Tangential filtration | Tangential filtration | Reference R. Diaz, 1981 | Reference R. Diaz, 1981; Reference to B. Urmeneta, et al, 1998 | Centrifugation | Collection with hoes |
| Harvest washing technique | does not apply | 2 washes in saline solution | Reference R. Diaz, 1981 | Reference R. Diaz. 1981; Reference to B. Urmeneta, et al, 1998 | does not apply | 1-2 washes in saline solution (6000 rpm for 30 minutes) |
| Solution to resuspend the harvest | Distilled water | does not specify | Reference R. Diaz, 1981 | Reference R. Diaz, 1981; Reference to B. Urmeneta, et al, 1998 | Distilled water | Saline solution |
| Post-harvest inactivation method | Sterilization at 120° C., 15 minutes | does not specify | Reference R. Diaz, 1981. | Reference R. Diaz, 1981; Reference to B. Urmeneta, et al, 1998 | Sterilization at 120° C.,15 minutes | Sterilization of 120° C., 15 pounds, 25 minutes |
| Extraction and Precipitation Method | does not apply | Hot water 100° C. | Reference R. Diaz. 1981 | Reference K. Diaz, 1981; Reference to B. Urmeneta, et al, 1998 | does not apply | does not apply |
| | Centrifugation: 12000 g, for 15 minutes | does not specify | Reference R. Diaz, 1981 | Reference R. Diaz, 1981; Reference to B. Urmeneta, et al. 1998 | Centrifugation | Centrifugation: 6000 rpm for 30 minutes |
| | 3X-Ethanol for 18 hours at 4° C., with stirring | 3X-Ethanol for 18 hours at 4° C., with stirring | Reference R. Diaz, 1981 | Reference R. Diaz, 1981; Reference to B. Urmeneta, et al, 1998 | 3X-Ethanol for 18 hours at 4-8° C., with stirring | 3X -Ethanol for 18 hours of 4° C., with stiring |
| | Centrifugation: 5000 g. for 10 minutes, at 4° C. | does not specify | Reference R. Diaz, 1981 | Reference R. Diaz, 1981; Reference to B. Unmeneta, et al, 1998 | Centrifugation | Centrifugation: 6000 rpm for 30 minutes |
| | 2X-Ethanol for 18 hours at −20° C. | 2X-Ethanol by O/N at −20° C. | Reference R. Diaz, 1981 | Reference R. Diaz. 1981; Reference to B. Unmeneta, et al, 1998 | 2X-Ethanol for 18 hours at −20° C. | 2X-Ethanol for 18 hours at −20° C. |
| | Centrifugation: 5000 g, for 5 minutes, at 5° C. | does not specify | Reference R. Diaz, 1981 | Reference R. Diaz, 1981; Reference to B. Urmeneta, et al, 1998 | Centrifugation | Centrifugation: 6000 rpm for 30 minutes |
| Solution to resuspend the NH antigen pellet | does not specify | does not specify | Reference R. Diaz, 1981 | Reference R. Diaz, 1981; Reference to B. Urmeneta, et al. 1998 | does not specify | Saline solution |
| Purification | Dialysis against distilled water | Digestion with nucleases and proteinase K | Reference R. Diaz, 1981 | Reference R. Diaz, 1981; Reference to B. Urmeneta, et al, 1998 | Dialysis against distilled water | RAW NATIVE HAPTEN (WITHOUT PURIFICATION PROCESS) |
| | | Ultracentrifugation 200,000 g, 6 h, 10° C. | Reference R. Diaz, 1981 | Reference R. Diaz, 1981; Reference to B. Urmeneta, et al, 1998 | | |
| | | Chromatography | Reference R. Diaz, 1981 | Reference R. Diaz. 1981; Reference to B. Urmeneta, et al, 1998 | | |
| | | Dialysis | Reference R. Diaz, 1981 | Reference R. Diaz, 1981; Reference to B. Jrmeneta, et al, 1998 | | |

-continued

| | | | | | | |
|---|---|---|---|---|---|---|
| | | | Reference R. Diaz, 1981. | Reference R. Diaz, 1981; Reference to B. Urmeneta, et al, 1998 | | |
| | | | Reference R. Diaz, 1981. | Reference R. Diaz, 1981; Reference to B. Urmeneta, et al, 1998 | | |
| | | | Reference R. Diaz, 1981 | Reference R. Diaz, 1981; Reference to B. Urmeneta, et al, 1998 | | |
| | | | Reference R. Diaz, 1981 | Reference K. Diaz, 1981; Reference to B. Urmeneta, et al 1998 | | |
| | | | Reference R. Diaz, 1981 | Reference R. Diaz, 1981; Reference to B Urmeneta, et al, 1998 | | |
| | | | Reference R. Diaz, 1981 | Reference R. Diaz, 1981; Reference to B. Urmeneta, et al, 1998 | | |
| | | | Reference R. Diaz, 1981 | Reference R. Diaz, 1981; Reference to B Urmeneta, et al, 1998 | | |
| | | | Reference R. Diaz, 1981 | Reference R. Diaz, 1981; Reference to B. Urmeneta, et al, 1998 | | |
| | | | Reference R. Diaz, 1981 | Reference R. Diaz, 1981; Reference to B. Urmeneta, et al, 1998 | | |
| | | | Reference R. Diaz, 1981 | Reference R. Diaz, 1981; Reference to B. Urmeneta, et al, 1998 | | |
| | | | Reference R. Diaz, 1981 | Reference R. Diaz, 1981; Reference to B. Urmeneta, et al, 1998 | | |
| | | | Reference R. Diaz, 1981. | Reference R. Diaz, 1981; Reference to B. Urmeneta, et al, 1998 | | |
| | | | Reference R. Diaz, 1981. | Reference R. Diaz, 1981; Reference to B. Urmeneta, et al, 1998 | | |
| Lyophilization of the antigen | Yes | Yes | does not specify | does not specify | Yes | Yes |
| | | | Sensitization | | | |
| Antigen concentration per ml of diluent | does not apply | 2.5 μg/ml | does not apply | 2.5 μg/ml | does not apply | 20 μg/ml |
| Diluent | | CABI pH 9.6; PBS 7.2 | | PBS | | CABI |
| Volume of antigen dilution per well | | does not specify | | does not specity | | 50 μl |

-continued

| | | | | | | |
|---|---|---|---|---|---|---|
| Antigen concentration per well | | does not specify | | does not specify | | 1 µg |
| 1st incubation | | Over Night 37° C.; 4° C. | | Over Night 4° C. | | Over Night 4° C. |
| 1st wash solution | | 98S Tween 20 (0.05%) | | PBS Tween 20 (0.05%) | | PBS Tween 20 (0.05%) |
| Number of washes | | 4 | | 3 | | 4 |
| Volume of wash solution per well | | does not specify | | does not specify | | 250 µl |
| Blocking solution | | does not specify | | does not specify | | Sol 3% skim milk |
| 2nd Incubation | | does not specify | | does not specify | | 1 h at 37° C. |
| 2nd wash solution | | does not specify | | does not specify | | PBS Tween |
| Number of washes | | does not specify | | does not specify | | 20 (0.05%) |
| Volume of wach solution per well | | does not specify | | does not specify | | 250 µl |
| Storage | | 4° C. | | does not specify | | 2-8° C. |
| | | | Preparation of sample | | | |
| Type of sample | Stood serum | Blood serum | Blood serum | Blood serum | Blood serum | Blood serum and milk (serum or whole, tank or per animal) |
| Sample treatment | does not apply | does not apply | does not apply | does not apply | does not apply | does not apply |
| Sample Predilution | | Yes | | Yes | | Yes |
| Sample quantity | | does not specify | | does not specify | | 15 µl |
| Sample diluent | | PBS Tween 0.05% | | PBS Tween 0.05% | | CABI |
| Amount of diluent | | does not specify | | does not specify | | 285 µl |
| | | | Challenge | | | |
| Amount of diluted sample per well | does not apply | 100 µl | does not apply | 100 µl | does not apply | 50 µl |
| Competitive Specifications of Competitive ELISA | | does not apply | | does not apply | | does not apply |
| Final volume per well | | does not specify | | does not specify | | 50 µl |
| Incubation | | 1 h 37° C. | | 1 h 37° C. | | 1 h 37° C. |
| | | | Washes | | | |
| Wash solution | does not apply | PBS Tween 0.05% | does not apply | PBS Tween 0.05% | does not apply | PBS Twaan 0.05% |
| Number of washes | | 4 | | 3 | | 4 |
| Volume of wash solution per well | | does not specify | | does not specify | | 250 µl |
| | | | Conjugate | | | |
| Conjugate | does not apply | IgG anti-sheep (rabbit); IgG anti-bovine; IgG anti-ruminant; Recombinent G protein | does not apply | Recombinant G protein | does not apply | IgG anti-bovine (goat) |
| Conjugate diluent | | PBS Tween (0.05%) | | PBS Tween (0.05%) | | CABI |
| Conjugate Concentration | | IgGs: 1:1000-1:2000; G protein: 0.2 µg/ml | | 0.2 µg/ml | | 1:2000 |
| Final conjugate volume per well | | 100 µl | | 100 µl | | 50 µl |
| Incubation | | 1 h 37° C. | | 1 h 37° C. | | 1 h 37° C. |
| | | | Washes | | | |
| Wash solution | does not apply | does not specify | does not apply | PBS Tween | does not apply | PBS Tween 0.05% |
| Number of washes | | dices not specify | | 3 | | 4 |
| Volume of wash solution per well | | does not specify | | does not specify | | 250 µl |
| | | | Substrate | | | |
| Substrate Name | does not apply | ABTS 0.1% | does not apply | ABTS | does not apply | ABTS |
| Substrate Diluent | | 0.05M citrate buffer (pH 4.0) and 0.004% H2O2 | | 0.05M citrats buffer (pH 4.0) and 0.004% H2O2 | | does not apply |
| Amount per well | | 100 µl | | does not specify | | 50 µl |
| Substrate incubation conditions | | 15 min, 20° C. | | 30 min, 20° C . | | 15 min, 20-23° C. in the dark |

-continued

| | | | | | | |
|---|---|---|---|---|---|---|
| Stop the reaction | | | | | | |
| Stop solution | does not apply | does not specify | does not apply | does not apply | does not apply | SDS 4% |
| Quanity | | does not specify | | | | 50 μl |
| Stability time | | does not specify | | | | 30 min |
| Reading of Optical Densities | | | | | | |
| Nanometers | does not apply | 405 | does not apply | does not specify | does not apply | 405 |
| Lyophilization of controls | | | | | | |
| Optical density for Positive control selection | does not use it | does not use it | does not use it | does not use it | does not use it | ≥1.0 |
| Optical density for Negative control selection | does not use it | does not use it | does not use it | does not use it | does not use it | 0.20-0.28 |
| Use of the lyophilization process for Negative Control and Positive Control | does not use it | does not use it | does not use it | does not use it | does not use it | Use of the Lyophilization process for Negative Conbol and Positive Control |

Work Done on the KIT Application:

In a study done in 2005 by a group of international researchers (including Dr. Bruno Garin-Bastuji, representative of the Reference Laboratory for Brucellosis in the European Union and of OIE/FAO) they used the Native Hapten ELISA with great success and recognizes that serological tests that detect anti-LPS-O antibodies could generate "False Positives" by cross-reactions with other Gram-negative bacteria including: *Vibrio cholerae, Escherichia coli* O: 157, *Salmonella* and *Yersinia enterocolitica O:* 9, being *Yersinia* the most frequent and significant "false positive", since their levels of anti-LPS-O antibodies in serum and milk that cross with *Brucella*, are usually high, persistent and fluctuating. The cross reaction between *Yersinia* and *Brucella* is due to its strong similarity of their LPS-O chains. This study referenced 68 scientific articles, and recognizes up to 15% of "false positives" in free zones of the European Union and that, in advanced eradication programs, a differential diagnosis is required with a confirmatory test different from LPS-O [31].

The KIT, motive of the present application, has already been field tested in diverse and different statistical designs. One of these studies was a complete production cycle, with a length of twelve (12) months, at a stable of 2,533 milking cows (100%) in production located in Torreón, Coahuila, Mexico, a high brucellosis incidence region, all the conventional tests that measure anti-LPS-O, both in blood serum and milk, were performed. These conventional tests generated a total of 741 positive animals, that is, 29.25% of the cows in production.

In half of these animals, this positivity to LPS-O was Fluctuating during the 12 months of length of the study.

This KIT was used as a confirmatory test, through which the response to a second specific brucellosis antibody, Native Hapten, was measured, resulting in 15.24% of "False Positives" (386 animals) generated by cross-reaction with other bacteria, and 14.02% of truly infected animals (355 animals positive to anti-NH ELISA KIT).

The 15% of "False Positives" emitted by all the conventional tests that measure anti LPS-O, in blood serum or milk, generates a great economic loss for cattle breeding in the world.

Results are shown in FIG. 5.

During this twelve month of the study the milk tank of 2,533 cows in production was monitored weekly, using a commercial ELISA and the milk ring test (MRT), both tests measure antibodies against LPS-O, and give the same "False Positives" in a fluctuating way. The milk was also confirmed with the KIT of the present application, which allowed corroborating the presence of anti-Native Hapten antibodies. Therefore, using this KIT for milk tank monitoring allows us to identify milk truly infected with brucellosis, discarding "False Positive" milk due to cross reactions with other bacteria.

BEST METHOD FOR CARRYING OUT THE INVENTION

Raw Native Hapten

The extraction of NH was made with the traditional method mentioned in literature of the present application. The antigen pellet was re-suspended in saline and tested crude (without purification) by RID and indirect anti-NH ELISA tests with positive blood sera confirmed with the official tests of NOM-041-ZOO-1995. In this assay, favorable results were obtained, so it was decided to test the crude extract with milk samples in indirect anti-NH ELISA test, where a favorable result was also obtained. Therefore, it was concluded that antigen purification is not necessary for plate coating.

NH Concentration

Different antigen dilutions were made, microplates were coated with those antigens, sera were tested and it was found the best concentration to coating. The ELISA test standardization was carried out by titration with the Native Hapten antigen (NH) to determine the optimal concentration of the antigen with which the microplates should be coated.

The antigen titration was based on the optimal antigen concentration of Radial Immunodiffusion (RID) test, which is 2 mg/mL. From this concentration, a series of dilutions was performed (1:2, 1:4, 1:8, 1:16, 1:32, 1:64, 1:100 and 1:128) with CABI buffer. 50 μl of each dilution of the antigen were added to the plate, i.e. distributing one dilution per line, so that each dilution was present in 12 wells of the plate. Subsequently, the coating protocol was continued.

Four samples of positive sera and 4 samples of negative sera were selected, which were tested in ELISA for triplicate. From the absorbance obtained, the mean absorbance of the positive and negative sera were obtained to establish the threshold that allowed differentiating negative absorbance from positive ones.

The criteria used was the following: To consider a sample as positive, the optical density reading was above the range of the negative's average plus three standard deviations (0.5432+3 (0.1521)=0.9995). Taking this cut-off as a reference, it was determined that the optimal antigen concentration in the plate corresponds to the value that best approaches to the optical density of 0.9995, minus one antigen dilution. Thus establishing the dilution 1:100 in the case of the antigen which corresponds to 1 microgram per well.

Use of Anti-Bovine IgG (Goat)

To search for the best secondary antibody, we reviewed the literature cited above, where we found reports on different types of immunoglobulins used in ELISA methods in different animal species, including bovine. It was determined that to obtain a better efficiency of the test directed to bovines it is necessary to use an anti-bovine IgG.

Native Hapten in Milk

In order to determine the minimum point of detection of positive milk in a negative milk tank, 92 dilutions were made, starting with a ratio of 1:1 of positive milk diluted in negative milk. The positive milk sample came from a cow confirmed as positive to *Brucella*, with the highest positivity presented in the Ring Milk test, RBT, Rivanol (1:400), Radial Immunodiffusion (RID) and indirect ELISA with NH. These anti-NH ELISAs were performed in both blood serum and milk serum. The negative milk was obtained from a pool of nine cows negative to all the tests mentioned before.

Of the 92 dilutions tested, the indirect anti-NH ELISA was able to detect the positivity level until the dilution number 27 corresponding to 969,162 liters of positive milk within a milk tank containing a volume of 29,030,838 liters of negative milk, giving a total of 30,000 liters. The positivity of the 27 dilutions studied was confirmed by the Ring Milk test, demonstrating the efficiency of the test for this type of samples.

Optical Density Range (DO) of Controls and their Lyophilization Process

The controls obtained from samples of blood serum and milk from animals were preselected based on their clinical story and positive or negative result at the official tests of Rose of Bengal (RBT), Rivanol, and Ring Milk (RMT), as well as in; fluorescence polarization assay (FPA) and Radial Immunodiffusion (RID).

Indirect anti-NH ELISA tests were performed on the selected sera, and based on the results, we selected the samples that showed an absorbance ≥1,000 for positive control and 0.20-0.28 for negative control. Two pools of sera were formed, one pool for positive control and the other for negative control, to which the official tests, RID and indirect ELISA were made, to confirm their positivity and negativity. Once the control pools were approved, they were subjected to lyophilization.

Two vials of freeze dried controls were taken, one positive and the other negative. They were resuspended with 1 mL sterile tridestilated water, and homogenized perfectly. To check control's stability once resuspended, they were analyzed by the official serological tests established by the norm NOM-041-ZOO-1995 as well as RID and the indirect anti-NH ELISA tests. Those tests were performed every 15 days. Said resuspended controls were kept under refrigeration at 4° C.

The stability of the controls was confirmed observing a concordance of 1 (one) between the 5 tests, that is, the positive control was positive to the 5 tests and the negative control was negative to the 5 tests. Finding that the optical densities were stable.

Kit Solutions Preparation

Preparation of Culture Medium and Solutions

The solutions to develop the kit are prepared with the procedure described below.

Tripticase Soy Agar (TSA) Medium: To prepare 1 L of TSA medium. Weigh 40 g/L of TSA and dissolve in 1 L of distilled water, the medium must be dissolved by heat until boil, then sterilized in an autoclave at 120° C. and 15 lbs. For 15 minutes. Once sterilized the medium is allowed to cool and before solidifying it is poured into Petri dishes, pouring approximately 5 mm thick into each plate. The well-sealed plates are allowed to solidify and stored at 4° C. The latter must be worked in a laminar flow cabinet, or in the presence of a Fisher burner.

Saline solution (NaCl 0.9%): To prepare 1 L of saline solution. Weigh 9 g of sodium chloride and dissolve it in 1 L of distilled water, mixing perfectly. Sterilize in autoclave at 120° C. and 15 lb. for 15 minutes.

Blocking solution: A solution of 3% skim milk is prepared. Weighing 3 g of skimmed milk powder and dissolve in 100 ml of sterile distilled water, mix perfectly to dissolve completely.

Sample Diluent Solution (10×) and Conjugate Diluent Solution (1×). Carbonate-Bicarbonate Buffer (CABI): A CABI buffer at pH of 9.6 is used as diluent. To prepare the solution at a 10× concentration, (the amounts at 1× change in proportion): Weigh 35.6 g of sodium carbonate (Na2CO3) and dissolve with distilled water. Add 84 g of sodium bicarbonate (NaHCO3) and dissolve. Add 2 g of sodium azide (NaN3) as preservative and dissolve. Adjust the pH of the solution to 9.6, using hydrochloric acid (HCl) or sodium hydroxide (NaOH).

Gauge to 1 L using a volumetric flask, and filter the solution with filter paper. Sterilize in an autoclave at 120° C. and 15 lb for 15 minutes and label with name, batch number and date of manufacture.

Washing Solution (10×). PBS-Tween 20 (0.05%): Weigh 14.4 g of Sodium hydrogen phosphate (Na2HPO4) and dissolve in distilled water using a stirrer. Weigh 2.2 g of Potassium dihydrogen phosphate (KH2PO4) and add it, stir until it dissolves perfectly. Add more water if necessary. Add 2 g of potassium chloride (KCl) and dissolve perfectly. Add 80 g of sodium chloride (NaCl) to the solution and stir until it is perfectly dissolved, the solution should remain crystalline. Adjust the pH of the solution to 7.4, using hydrochloric acid or sodium hydroxide. Gauge to 1 L and shake the solution well. Filter the solution using filter paper and sterilize in an autoclave at 120° C. and 15 lb. for 15 minutes. Upon cooling, add 5 ml of tween-20, shaking gently. Pour into a bottle and label the bottle with name, batch number and date of manufacture.

Stop solution. SDS 4%: 4% sodium dodecyl sulfate (SDS) is used as a stop solution. Weigh 40 g of SDS. Mix with distilled water until it dissolves completely and gauge the solution at 1 L. If it does not dissolve completely, heat the solution until it is warm, at approximately 37° C. until it dissolves perfectly. Sterilize in an autoclave at 120° C. and 15 lb. for 15 minutes. Pour in a bottle and label with name, batch number and date.

Substrate: A 2,2'-azino-bis(3-ethylbenzothiazoline-6-sulphonic acid) (ABTS) commercial solution is used as substrate.

REFERENCES

1. Brucellosis. Medical microbiology. INRA. 28:512-525.
2. Arzola, V. E. A., Gonzalez, M. A., González, J. L. I., Hernández, M. L., Aparicio, E. D., Moorillón, G. V. N., & River, B. E. (2012). Diagnóstico rápido y efectivo de brucelosis bovina en sangre, mediante una reacción en cadena de la polimerasa doble. Revista Mexicana de Ciencias Pecuarias, 46(2), 147-158.
3. Aparicio, E. D. (2013). Epidemiologia de la brucelosis causada por *Brucella melitensis, Brucella suis* y *Brucella abortus* en animales domésticos. Revue Scientifique et Technique, 32(1), 43-51.
4. Esperanza Gonzalez, M., Hernández Andrade, L., & Díaz Aparicio, E. (2006). Prueba de inmunodifusión radial con hapteno nativo para diferenciar bovinos con revacunaciones repetidas con la cepa S19 de *Brucella abortus,* 44, 269-276.
5. E. Herrera López, L. Hernández Andrade, G. P. R. and E. D. A. (2007). Study of Brucellosis Incidence in a Bovine Dairy Farm Infected with *Brucella abortus*, Where Cattle Was Revaccinated with RB51. International Journal of Diary Science. 2(1): 50-57.
6. Herrera, E., Palomares, G., & Diaz-Aparicio, E. (2008). Milk production increase in a dairy farm under a six-year brucellosis control program. Annals of the New York Academy of Sciences, 1149, 296-299.
7. Leal-hernández, M., Jaramillo-meza, L., & Hernández-andrade, L. (2007). Producción de interferón gamma en cultivos de sangre completa en respuesta a antigenos de *Brucella abortus* en bovinos vacunados con RB51 Production of interferon gamma in whole blood cultures in response to *Brucella abortus* antigens in RB51-vaccinated cat, 45(2), 147-159.
8. Maria Dolores Fuentes Delgado, Irene V. Vitela Mendoza, Beatriz Arellano-Reynoso, Rigoberto Hernández Castro, José Francisco Morales Álvarez, Carlos Cruz-Vazquez. (2007). Presence of *Brucella abortus* vaccinal strain RB51 in Vaginal Exudates of abortaded cows. Research Journal of Dairy Sciences, 1 (1-4): 13-17.
9. Aparicio-Bahena, A., Diaz-Aparicio, E., Hernández-Andrade, L., Pérez-González, R., Alfonseca-Silva, E., & Suárez-Güemes, F. (2003). Evaluación serológica y bacteriológica de un hato bovino con brucelosis y revacunado con dosis reducida de *Brucella abortus cepa* 19. Técnica Pecuaria, 41(2), 129-140.
10. A., Castro, A., González, H. A; Prat, S. R.; & Baldi, P. C. (2006). Detección de anticuerpos anti-*Brucella* spp. en cerdos mediante técnicas de aglutinación y ELISA indirecto en las provincias de Buenos Aires y La Pampa, Argentina. Revista Argentina de Microbiologia, 38: 75-78.
11. Kittelberger R, Hilbink F, Hansen M F, Penrose M, de Lisle G W, Letesson J J, et al. Serological crossreactivity between *Brucella abortus* and *Yersinia enterocolitica* 0:9. Immunoblot analysis of the antibody response to *Brucella* protein antigens in bovine brucellosis. (1995). Vet Microbiol; 47: 257-70.
12. Rodriguez, A., Orduña, A., Ariza, X., Morivon, I., Diaz, R., Blasco, J., Almaraz, A., Martinez, F., Ruiz, C. y Abad, R. (2001). Manual de Brucelosis. Ed. Junta de Castilla y Leon. Copyright. Zamora, España.
13. Abernethy D. A., Moscard-Costello J., Dickson E., Harwood R, Burns K., McKillop E., McDowell S, & Pftffer D. U. (2011).—Epidemiology and management of a bovine brucellosis cluster in Northern Ireland. Prev. vet. Med., 98 (4), 223-229.
14. Bustamante Sanchéz, J., Hernández Salazar, I., Díaz, A. E., Mazano Cañas, C., Pérez González, R., & Andrade, L. H. (2000). Estudio Bacteriológico Y Serológico De Brucelosis en vacas revacunadas con dosis reducida de *cepa* 19 de *Brucella abortus*. Inifap, (5).
15. Cantú, A., Díaz, E., Andrade, L. H., Adams, G. L., & Güemes, F. S. (2007). Estudio epidemiológico de un hato bovino con prevalencia media de brucelosis, vacunado con las mutantes rugosas de. Group, 38(2), 197-206.
16. Diaz, R, P. Garatea, L. M. Jones, and I. Moriyon. (1979). Radial immunodiffusion test with a *Brucella* polysaccharide antigen for differentiating infected from vaccinated cattle. J. Clin. Micro-biol. 10:37-41.
17. Moriyón UI. *Brucella* cell structure. In: Memory to 50th Anniversary Meeting of Brucellosis Research Conference. Chicago ILL, USA Nov. 8-9, 1997: 3-18.
18. Moriyon, I. et al. (1998). Structure and properties of the outer membranes of *Brucella abortus* and *Brucella melitensis*. Internatl Microbiol, 19-26.
19. Alonso-Urmeneta, B., Moriyon, I., & Blasco, J. M. (1988). Enzyme-linked immunosorbent assay with *Brucella* native hapten polysaccharide and smooth lipopolysaccharide. Journal of Clinical Microbiology.
20. Dubray, G. (1984). Progrès récents sur la biochimie et les pro-priétés biologiques des antigènes de *Brucella*. Dev. Biol. Stand. 56:131-150.
21. Stemshorn, B. W. (1984). Recent progress in the diagnosis of brucellosis. Dev. Biol. Stand. 56:325-340.
22. Organizacion Mundial de Sanidad Animal. (2000). Brucelosis bovina, 1-8.
23. Diaz, R., Toyos, J., Salvó, M. D., & Pardo, M. L. (1981). A simple method for the extraction of polysaccharide B from *Brucella* cells for use in the radial immunodiffusion test diagnosis of bovine brucellosis. Annales de Recherches Veterinaires. Annals of Veterinary Research, 12(1), 35-39.
24. Fernandez-Lago, L., & Diaz, R. (1986). Demonstration of antibodies against *Brucella melitensis* 16M lipopolysaccharide and native hapten in human sera by enzyme-linked immunosorbent assay. Journal of Clinical Microbiology.
25. Alonso-Urmeneta, B., Moriyon, I., & Blasco, J. M. (1988). Enzyme-linked immunosorbent assay with *Brucella* native hapten polysaccharide and smooth lipopolysaccharide. Journal of Clinical Microbiology, 26(12), 2642-2646.
26. Diaz-Aparicio E, Aragon V, Marin C, Alonso B, Font M, Moreno E, et al. Comparative analysis of *Brucella* serotype A and M and *Yersinia enterocolitica O:9* polysaccharides for serological diagnosis of brucellosis in cattle, sheep, and goats. J Clin Microbiol. 1993; 31(12):3136-41.
27. Diaz-Aparicio, E., Marin, C., Alonso-Urmeneta, B., Aragón, V., Pérez-Ortiz, S., Pardo, M., Moriyón, I. (1994). Evaluation of Serological Tests for Diagnosis of *Brucella melitensis* Infection of Goats. Journal of Clinical Microbiology, 32(5), 1159.
28. Diaz-Aparicio, E., Uria, I. M., Blasco-Martinez, J. M., Marin-Alcala, C., & Diaz, R. (1996). Diagnóstico de *Brucella melitensis* en ovinos usando inmunodifusion radial con hapteno nativo. Técnica Pecuaria En México, 34(2), 99-103.
29. Alonso-Urmeneta B, Marin C, Aragón V, Blasco J M, Diaz R, Moriyón I. Evaluation of lipopolysaccharides and polysaccharides of different epitopic structures in the indirect enzyme-linked immunosorbent assay for diagnosis of brucellosis in small ruminants and cattle. Clin Diagn Lab Immunol [Internet]. 1998; 5(6):749-54.

30. Marin, C. M., Moreno, E., Moriyón, I., Diaz, R., & Blasco, J. M. (1999). Performance of competitive and indirect enzyme-linked immunosorbent assays, gel immunoprecipitation with native hapten polysaccharide, and standard serological tests in diagnosis of sheep brucellosis. Clinical and Diagnostic Laboratory Immunology, 6(2), 269-272.

31. Muñoz, P. M., C. M. Marín, D. Monreal, D. Gonzalez, B. Garín-Bastuji, R. Diaz, R. C. Mainer-Jaime, I. Moriyón, and J. M. Blasco. (2005). Efficacy of Several Serological Tests and Antigens for Diagnosis of Bovine Brucellosis in the Presence of False-Positive Serological Results Due to *Yersinia* enterolitica O:9 American Society for Microbiology. Clin Diagn Lab Immunol [Internet]. 2005; 12(1):141-51.

32. WO2008051065 A1, fecha de presentación: Oct. 16, 2007. Fecha de publicación: Mayo 2, 2008. Universidad Autónoma de Nuevo León. https://www.google.com/patents/WO2008051065A1?cl=es

BRIEF FIGURES DESCRIPTION

FIG. 1 shows the flow diagram of the Native Hapten antigen obtaining process. From the *B. melitensis* 16M strain cultivation, the cell harvest and the antigen extraction until the lyophilization process of the antigen obtained.

Figure 2:
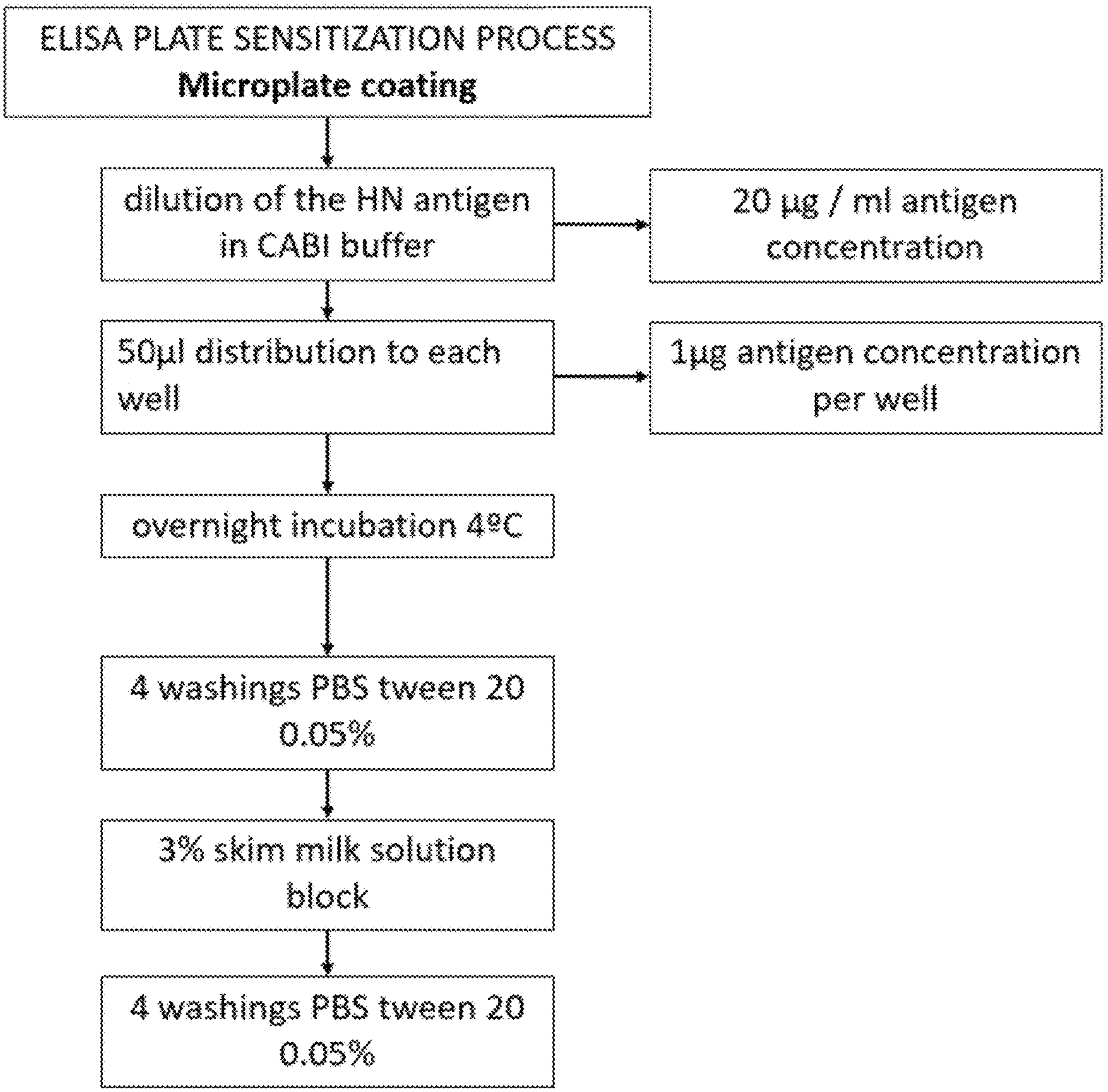
FIG. 2 shows the flow diagram of the antigen coating process of the ELISA plates. This diagram describes the steps that are carried out to coat the plates with the Native Hapten antigen.
Figure 3:
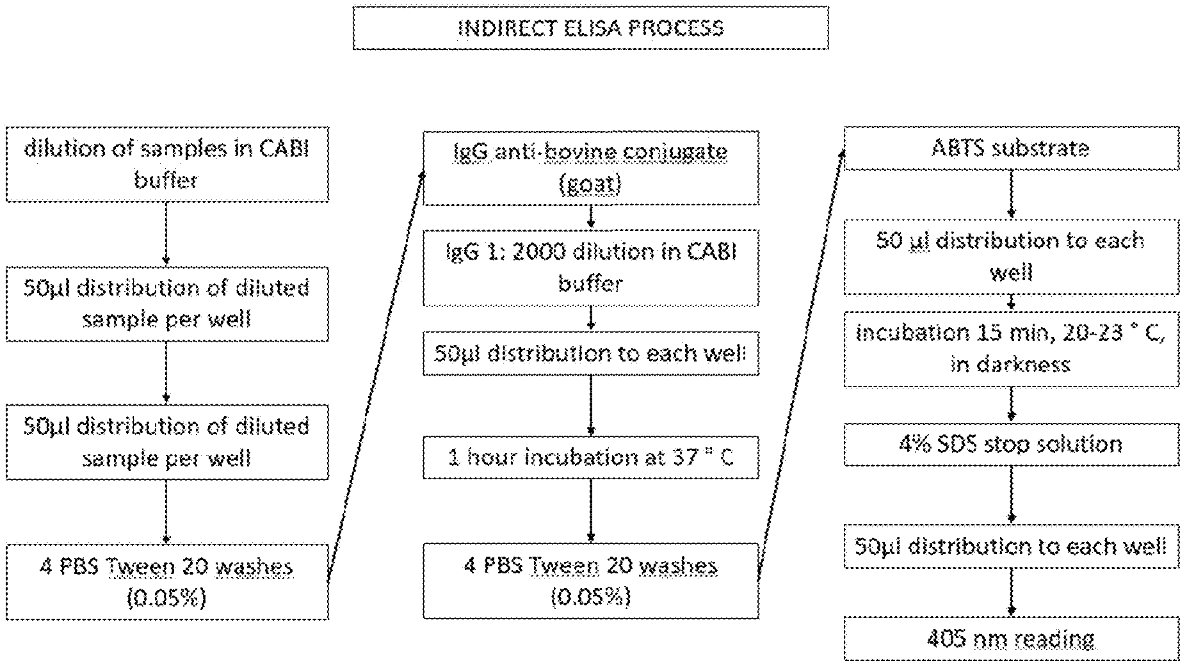
FIG. 3 shows the flow diagram of the indirect ELISA process, which describes the steps to be performed during the assay.
Figure 4:
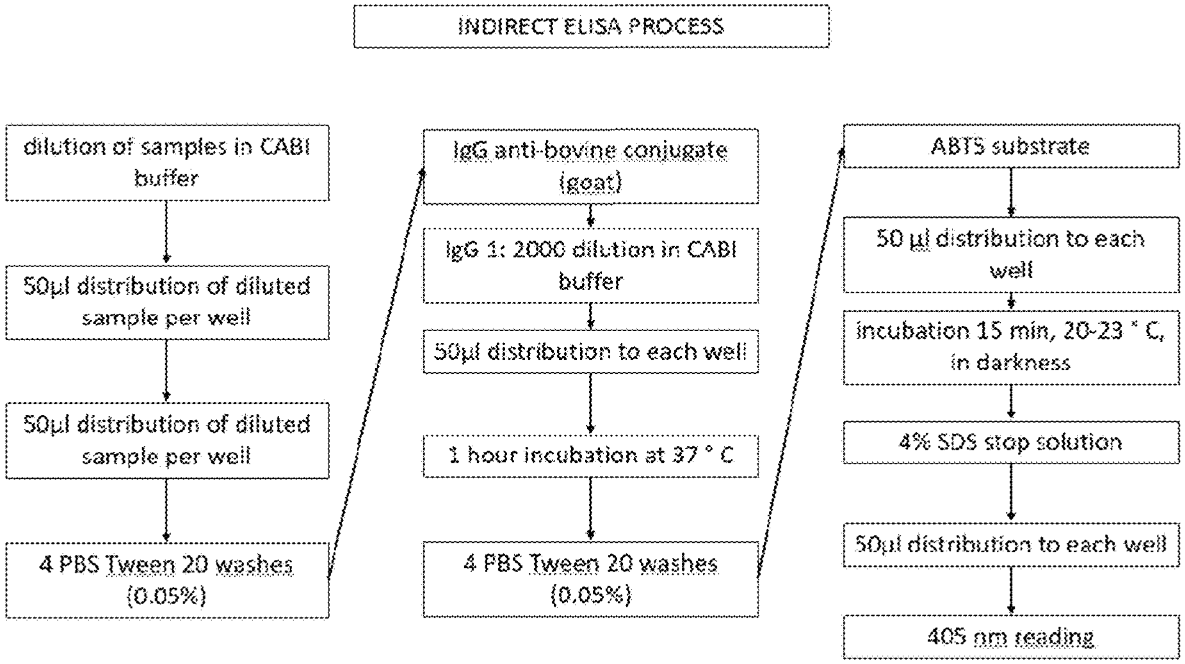
FIG. 4 shows the flow diagram of the blood serum controls and milk controls obtaining process. Showing the conditions by which the controls are selected and their validation before being freeze dried.
Figure 5:
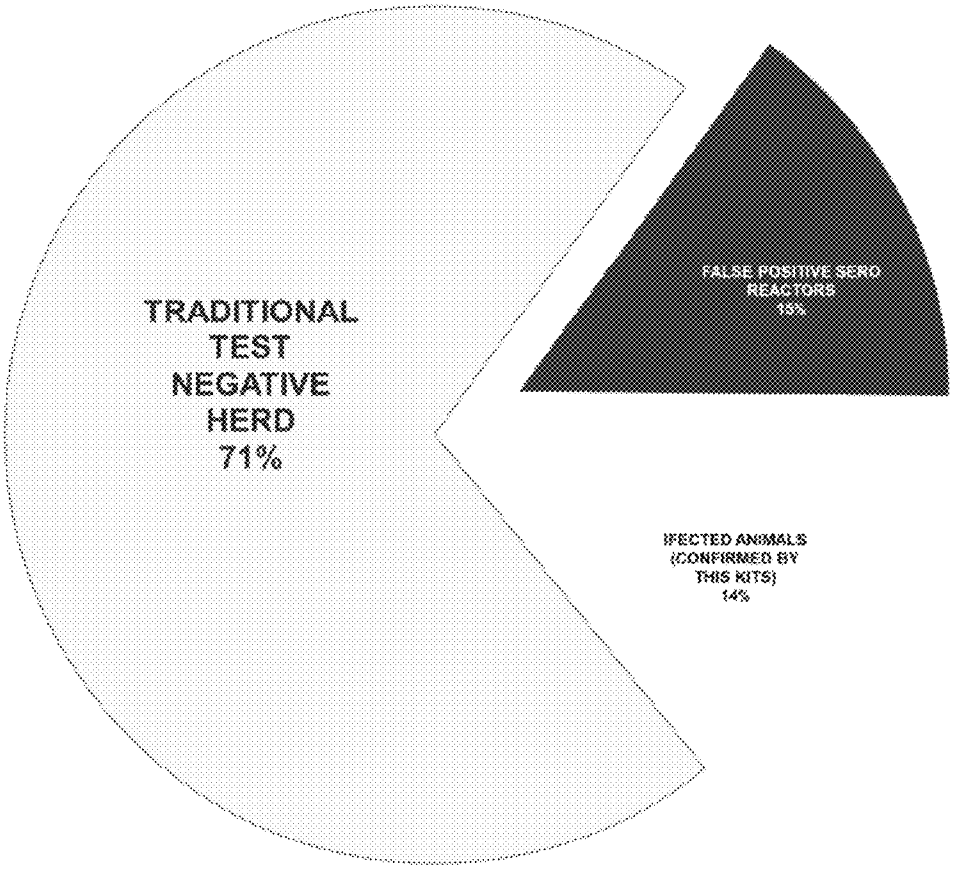
FIG. 5 shows the result on the use of this KIT in a herd with 2533 dairy cows in production, and their results to conventional tests, as well as the "False Positive" animals and those really infected.

The invention claimed is:

1. Indirect ELISA test procedure to detect antibodies anti Native Hapten for confirmatory diagnosis of bovine brucellosis in blood serum and individual milk (per animal) and bulk milk (tank) with a detection capacity of 969,162 liters of positive milk in a 30,000-liter tank, wherein the antigen Native Hapten is crude Native Hapten, which is obtained by the next procedure of extraction with ethanol from *B. melitensis* 16M strain, with no further purification treatment:

a. strain harvest is inactivated by heat in the autoclave, sterilizing at 120° C. and 15 lb. for 25 minutes;

b. waiting for it to cool down and perform a centrifugation at 6000 rpm for 30 minutes;

c. three volumes of cold ethanol are added to the supernatant;

d. placing the supernatant in magnetic stirring, maintaining it at 4° C. for 18 hours to precipitate the antigens; centrifuging the supernatant at 6000 rpm for 30 minutes, taking the pellet and resuspend in saline, adding 0.5 ml, mixing and observing the turbidity, if it is observed too saturated, adding 0.5 ml more, avoiding to reach transparency as this could dilute the antigen so that a low concentration of it will be obtained, this is labeled as LPS antigen (lipopolysaccharide);

e. two more volumes of cold ethanol are added to the supernatant, and it is kept in freezing (−20° C.) for 18 hours without agitation to precipitate the NH antigen;

f. when finished, centrifuge at 6000 rpm for 30 minutes;

g. the formed pellet is taken and resuspended in 0.5 ml of saline, observing the turbidity, and adding more saline solution if necessary;

h. This suspension contains the Crude Native Hapten antigen with no further purification treatment; and wherein the procedure further comprises the following steps:

i) coating of ELISA plates with the crude Native Hapten antigen, obtained in steps a through h, wherein the coating of ELISA microplates is performed with crude Native Hapten antigen at a 1 microgram per well concentration for confirmatory diagnosis of bovine brucellosis in blood serum and individual milk (per animal) and bulk milk (tank);

ii) producing lyophilized controls of blood serum and milk serum (whey) used as the reference for determining the cut-off point of the test, wherein positive controls have an absorbance of ≥1.0, and negative controls of 0.20-0.28; both at a wavelength of 405 nm;

iii) conducting Indirect ELISA process, which comprises:

Distributing 285 μL of a Sample Diluent Solution to each well in a pre-dilution Microplate, wherein the Sample Diluent Solution is a Bicarbonate Carbonate Buffer (CABI);

Adding 15 μL of Negative Control in wells A1 and B1; and 15 μL of Positive Control in wells C1 and D1, continuing adding 15 μL of the sample (blood serum or milk) in the remaining wells;

Taking 50 μL of the diluted samples and controls in the pre-dilution microplate and transferring them to the microplate coated with Native Hapten of step i);

Incubating the coated microplate for 1 hour at 37° C.;

Washing each well with 250 μL of the previously diluted Washing Solution, and making a total of 4 washes; wherein the washing solution is PBS-TWEEN 20;

Adding 50 μL of the previously diluted Conjugate (dilution 1:2000) to each well, wherein the conjugate is an anti-bovine IgG produced in goat conjugated with horseradish peroxidase;

Incubating the Microplate for 1 hour at 37° C.;

Performing 4 more washes;

Adding 50 μL of Substrate (ABTS) to each well;

Incubating the Microplate for 15 minutes at room temperature (20° C.-25° C.) in darkness;

Distributing 50 μL of a Stop Solution, wherein the stop solution is a solution of sodium dodecyl sulfate (SDS) at 4%; and Reading at 405 nm of optical, wherein the reading is stable for 30 minutes once the Stop Solution has been added.

2. A kit for indirect ELISA test, wherein the kit comprises the following components:

ten (10) microplates coated with 1 microgram per well concentration of antigen crude Native Hapten of claim 1; plate containing 96 wells (distributed in 12 strips of 8 wells each strip) of flat and clear bottom, with a surface treated specially for a high capacity of adhesion of the antigen, with a maximum capacity of 360 microliters per well;

five (5) microplates of 96 wells, without treatment, to perform the predilution of samples;

four (4) bottles of sixty (60) milliliters each with PBS-Tween 20 Washing Solution, 0.05%, at (10×) concentration;

one bottle (1) of forty (40) milliliters of Sample Diluent Solution, based on CABI (carbonate bicarbonate) Buffer at (10×) concentration;

one (1) bottle of fifty (50) milliliters of Conjugate Diluent, based on CABI (carbonate bicarbonate) buffer at concentration (1×);

one (1) 50 milliliter bottle of Substrate, which is ABTS (commercial product);

one (1) vial of one (1) milliliter consisting of 25 microliters of Concentrated Conjugate, which is an Immunoglobulin G-anti Bovine, conjugated with horseradish peroxidase produced in goat (commercial product) which is prediluted in a preservative HRP Protector, which is a peroxidases stabilizer;

one (1) bottle of fifty (50) milliliters of Stop Solution, which is sodium dodecyl sulfate (SDS) at 4% concentration;

one (1) freeze dried positive blood serum vial;

one (1) freeze dried negative blood serum vial;

one (1) freeze dried positive milk serum vial;

one (1) freeze dried negative milk serum vial; and wherein all control vials contain one (1) milliliter of freezed dried serum for reconstitution in one (1) milliliter of distilled water.

* * * * *